United States Patent
Hsu et al.

(10) Patent No.: US 6,383,525 B1
(45) Date of Patent: May 7, 2002

(54) HERBAL COMPOSITIONS FOR TREATING IMMUNOLOGICAL DISORDERS

(75) Inventors: Ching-Hsiang Hsu, Taibao; Shuenn-Jyi Sheu, Taipei, both of (TW)

(73) Assignee: GloboAsia L.L.C., Hanover, MD (US)

( * ) Notice: Subject to any disclaimer, the term of this patent is extended or adjusted under 35 U.S.C. 154(b) by 0 days.

(21) Appl. No.: 09/735,536

(22) Filed: Dec. 14, 2000

(51) Int. Cl.[7] .......................... A01N 65/00; A61K 35/78
(52) U.S. Cl. ..................... 424/728; 424/725; 424/757; 424/764; 424/773; 424/774
(58) Field of Search ................. 424/725, 757, 424/773, 774, 728, 764

(56) References Cited

U.S. PATENT DOCUMENTS

| | | |
|---|---|---|
| 4,886,666 A | 12/1989 | Liu |
| 5,190,757 A | 3/1993 | Kim |
| 5,225,203 A | 7/1993 | Kim |
| 5,281,583 A * | 1/1994 | Soma et al. .................. 514/23 |
| 5,595,743 A | 1/1997 | Wu |
| 5,908,628 A | 6/1999 | Hou |
| 6,200,570 B1 * | 3/2001 | Diwant et al. .............. 514/858 |

OTHER PUBLICATIONS

Derwent Computer Abstract 2000–476701 MA CN 1245695 Mar. 01, 2000.*
Derwent Computer Abstract 2000–073305 Chen et al CN 1203797 Jan. 06, 1999.*
Toda, Shizuo et al.; Effects of the Chinese Herbal Medicine "Saiboku–To" on Histamine Release from and the Degranulation of Mouse Peritoneal Mast Cells Induced by Compound 48/80; Journal of Ethnopharmacology, 1988, vol. 24, P 303–309.

Guizhen, Yang; Immunologic Effect of Traditional Chinese Drugs; Chinese Medical Journal, 1996, vol. 109(1), P 59–60.

Hamasaki, Y. et al.;The Chinese herbel medicine, Shin–pi–To, inhibits Ige–mediated leukotriene synthesis in rat basophilic leukemia–2H3 cells: Journal of Ethnopharmacology, 1997, vol. 56, P 131.

Zou, Jin–pan et al.;Clinical Study on Treating Asthma of Cold Type with Wenyang Tongluto Mixture; Chinese Western Medical Association Magazine, 1996, vol. 16, P 529–532.

Hsieh, K–H.; Evaluation of efficacy of traditional Chinese medicines in the treatment of childhood bronchial asthma: clinical trail, immunological tests and animal study; Pediatr Allergy Immunol, 1996, vol. 7, P 140.

* cited by examiner

Primary Examiner—Herbert J. Lilling

(57) ABSTRACT

The present invention provides pharmaceutical compositions which include Chinese herbs. These pharmaceutical compositions are especially effective in treating patients with immunological disorders, such as asthma, atopic eczema, atopic dermatitis, allergic rhinitis and rheumatoid arthritis. The pharmaceutical compositions contain ophiopogon (*Tuber Ophiopogonis*), pinellia (*Tuber Pinelliae*), raw licorice (*Radix Glycyrrhizae*), tang-shen (*Radix Codonopsitis*) or American ginseng (*Radix Pancis Quinquefolii*), and lantern tridax (*Herba Tridacis procumbentis*)/Taiwan adenostema (*Herba Adenostematis*)/ heartleaf houttuynia (*Herba houttuyniae*). So far, Taiwan adenostema, and heartleaf houttuynia have been found only in Taiwan. Lantern tridax has been found in Taiwan and South America.

24 Claims, 6 Drawing Sheets

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gaatgtacca ggagccatat c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
ctcagtacta cgagtaatcc a                                              21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
gttggataca ggccagactt tgttg                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
gattcaactt gcgctcatct taggc                                          25
```

HERBAL COMPOSITIONS FOR TREATING IMMUNOLOGICAL DISORDERS

FIELD OF THE INVENTION

The present invention relates to novel medicinal herbal compositions and their use for treating patients with immunological disorders, particularly IgE mediated diseases, which include, but are not limited to, allergic rhinitis, allergic conjunctivitis, allergic asthma, atopic eczema, atopic dermatitis, food allergy, hyper IgE syndrome, and rheumatoid arthritis. The present invention also relates to methods for making the medicinal herbal compositions and the method for treating patients with the medicinal herbal compositions.

BACKGROUND OF THE INVENTION

Antigen-induced, particularly allergen-induced immunological disorders, such as asthma, has long been known as one of the serious health problems in the world. Allergy in one form or another afflicts more than 20% of the world population. In recent years, statistics shows that the onset of the allergic-related immunological disorders has shifted to the younger population, which means that more children and/or adolescents have developed symptoms of allergen-induced immunological disorders. For instance, in Taiwan, the prevalence of childhood asthma increased from 1.3% in 1974, to 5.07% in 1985, and to 5.8% in 1991. Also, allergic rhinitis increased from 7.84% in 1985 to 20.67% in 1991. Furthermore, atopic eczema was 1.43% in 1974 and 1.23% in 1985, in 1991, it was 3.84%. It is believed that the early onset of allergen-related immunological disorders are likely due to environmental pollution.

Respiratory allergies are immunoglobulin E (IgE)-mediated immune response. (See Brinker, *J. Naturopathic Medicine,* (1993):4:64–68). There are two major types of respiratory allergic reactions: The immediate hypersensitivity reactions include allergic rhinitis (hay fever) and allergic (extrinsic) bronchial asthma. Allergic rhinitis is brought on by antigen/IgE binding to sensitized mast cells and basophils, causing a decrease in cAMP which leads to release of esosinophil chemotactic factor and histamine. Histamine binding to H1-receptors has several results. It increases vasodilation, capillary permeability, and smooth muscle contraction, manifesting as nasal congestion with watery discharge, sneezing, and itching eyes.

Allergic asthma is another IgE-mediated immune response in which mast cells release histamine, bradykinin, and arachidonic acid metabolites including the leukotriene slow reacting substances of anaphylaxis and thromboxane/ prostaglandin bronchoconstrictors. Platelet activating factor is another potent asthma mediator released from a number of leukocytes. In this condition, histamine, which released after a decrease in cAMP, acts on H1-receptors to cause bronchospasm. It is also responsible for bronchoconstriction due to cholinergic reflex action and half of the prostaglandin generation in anaphylaxis.

While the percentage of affected population and severity of the diseases are rising, current methods for treating allergy still primarily depend on empirical and serendipitous findings rather than from scientific approach. At present, most patients are treated with drugs that aim at controlling symptoms resulted from the release of mediators by effector cells. Although some drugs appear to be effective in short term and with few occurrences of adverse effects, long term effects for preventing disease progression and permanent destruction are still largely unknown. For example, long-term oral therapy, such as steroid therapy, for treating asthma, is now known to be associated with multiple debilitating effects such as growth delay, osteoporosis, and adrenal suppression.

Traditional Chinese herbs and medicinal combinations have been known for improving function of immune system and treating various chronicle immunological disorders. For example, Hamasaki et al., *J. Ethnopharmacology,* (1997) 56:123–131, disclose a Chinese herbal medicine, Shinpi-To, which inhibits IgE-mediated leukotriene synthesis in rat basophilic leukemia-2H3 cells. Shinpi-To is a freeze-dried granular Chinese herbal medicine prepared from extract of seven (7) medicinal herbs, i.e., *Ephedrae herba* (*Ephedra sinica* Stapf), *Armeniacae semen* (*Prunus armeniaca* Linne), *Magnoliae cortex* (*Magnolia obovata* Thunberg), *Aurantii nobilis Pericarpium* (*Citrus unshiu* Markovich), *Glycyrrhizae radix* (*Glycyrrhiza uvalensis* Fischer), *Bupleuri radix* (*Bupleurum falcatum* L.), and *Perillae herba* (*Perilla frutescens* Britton var. acuta Kudo). Shinpi-To is useful for treating childhood asthma.

Toda et al., *J. Ethnopharmacology,* (1988) 24:303–309, discloses a Chinese herbal medicine, Saiboku-To, which shows inhibitory effects on histamine release from mouse peritoneal mast cells. Saiboku-To is useful for treatment of asthma. Saiboku-To contains ten medicinal herbs: *Bupleurum falcatum* L., *Pinellia ternata* Breitenbach, *Poria cocos* Wolf, *Scutellaria baicalensis* Georgi, *Zizyphus vulgaris* Lam., *Panax ginseng* C. A. Meyer, *Magnolia oborata* Thumberg, *Glycyrrhiza glabra* L., *Perilllae frutescens* Britton var. acuta Kudo, and *Zingiber officinale* Roscoe.

Li et al., *Immunopharmacology,* (1999), 43:11–21, discloses a Chinese herbal medicine, Hochu-Ekki-To, which shows effects on restoring stress-induced immunosuppression. Hochu-Ekki-To consists of ten (10) ingredients, i.e., Ginseng Rx., *Atractylodis alba* Rz., Astragali Rx., *Angelicae sinensis* Rx., Jujubae Fr., *Citri reticulatae* Pc., Bupleuri Rx., Glycyrrhizae Rx. Preparata, Zingiberis recens Rz., and Cimicifugae Rz.

Zou et al., *Chinese Traditional and Western Medical Magazine,* (1996):529–532, discloses a Chinese herbal medicine, Wenyang Tongluo mixture, for treating cold-type asthma patients. It shows effects on improving pulmonary ventilation functions, regulating adrenergic β-receptors of peripheral blood lymphocytes, and decreasing the serum level of 5-hydroxytryptamine. Wenyang Tongluo mixture contains twelve (12) medicinal herbs, i.e., Red Ginseng, Zhi Fu Pian, Yin Yang Huo, Dried Ginger (*Zingiberis recens* Rz.), Zhi Huang Zhi, *Angelicae sinesis* Rx., Ephedra, Polygalae Rx., Sang Baipi, Sheng Shi Gao, *Schisandrae* Fr., and Licorice (*Glycyrrhizae* Rx. Preparata).

There is also an ophiopogon decoction disclosed on the internet (www.herb.com.tw) which shows a combination of six (6) herbs, i.e., *Ophiopogonis* Rx., *Pinelliae* Rz. Preparata, *Oryzae* Sm., *Jujubae* Fr., *Ginseng* Rx., and *Glycyrrhizae* Rx. It is useful for treating bronchitis and bronchial asthma.

In dealing with Chinese herbal medicine, it is critical to control the quality of the herbs, because the contents and/or active ingredients of the herbs can vary significantly due to herb's growing conditions and harvesting seasons/ techniques. If any of the critical conditions and factors, such as the locality where the herbs are grown, the season(s) when the herbs can be harvested, and the manufacturing process of the herb, are not met, the effectiveness of the herbal medicine would vary. So far, there has been no report showing the adoption of any reliable scientific method for monitoring the quality of the Chinese herbal medicine.

The present invention provides novel and non-toxic pharmaceutical compositions derived from herbs which are primarily found in China and Taiwan. The combined use of these herbs has never been found in any literatures or reports. These pharmaceutical compositions are particularly effective in treating patients with immunological disorders, especially IgE mediated diseases. The pharmaceutical compositions of the present invention have demonstrated special effects on down-regulation of the synthesis of interleukin 4 (IL-4) and suppression of IgE. In addition, to effectively control the quality of the herbs, the present invention fingerprints each herb using thin layer chromatography (TLC) and high performance liquid chromatography (HPLC) to ensure that each herb used in the composition contains consistent and reproducible ingredients.

SUMMARY OF THE INVENTION

The present invention provides pharmaceutical compositions which contains a variety of Chinese herbs. The pharmaceutical compositions contain, as essential herbs, Ophiopogon (*Tuber ophiopogonis*), Pinellia (*Tuber Pinelliae*), and raw Licorice (*Radix Glycyrrhizae*). The preferred weight ratio of ophiopogon: pinellia: raw licorice is 3:2:1. The fourth herb is either tang-shen (*Radix Codonopsitis*) or American ginseng (*Radix Pancis Quinquefolii*). The final herb is selected from a group of three (3) herbs which are lantern tridax (*Herba Tridacis procumbentis*), Taiwan Adenostema (*Herba Adenostemmatis*), and Heartleaf houttuynia (*Herba Houttuyniae*). Taiwan Adenosterma and Heartleaf houttuynia, can only be found in Taiwan. Lantern tridax can be found in Taiwan and South America. Among these pharmaceutical compositions, the most preferred composition contains ophiopogon, pinellia, raw licorice, American ginseng, and lantern tridax. The preferred weight ratio of ophiopogon:pinellia:raw licorice:tang-shen (or American ginseng):lantern tridax (or Taiwan Adenostema or heartleaf houttuynia) is 3:2:1:1:1.

The method for preparing the pharmaceutical composition is as follows: First, except for ophiopogon, all of the herbs are cut into pieces, dehydrated, ground, and passed through a sieve to produce herbal powder. The pharmaceutical ingredients in ophiopogon are extracted by boiling and condensing ophiopogon in water. The ophiopogon extract (filtrate) is then obtained by passing the condensed ophiopogon-water mixture through a sieve. Second, the ophiopogon filtrate is mixed with the herbal power to form a herbal mixture. This herbal mixture is then placed into a fluidized granulation machine for the production of granules. The granules can optionally be sieved to produce granules with uniform size. The granules can be further encapsulated. The pharmaceutical compositions are particularly effective in treating patients with immunological disorders, particularly IgE mediated diseases, which include, but are not limited to, allergic rhinitis, allergic conjunctivitis, allergic asthma, atopic dermatitis, food allergy, hyper IgE syndrome, atopic eczema, and rheumatoid arthritis.

Finally, the present invention employs a method to ensure the quality of the herbs used for the preparation of the composition. Each herb is fingerprinted using high performance liquid chromatography (HPLC). Therefore, if the quality of the herbs changes, such as due to growing conditions (too much rain or draught) or harvesting time, they can be detected by studying the profiles of the HPLC chromatograms. In addition to HPLC, a thin-layer chromatography (TLC) method is also adopted.

DETAILED DESCRIPTION OF THE INVENTION

Figure 1:
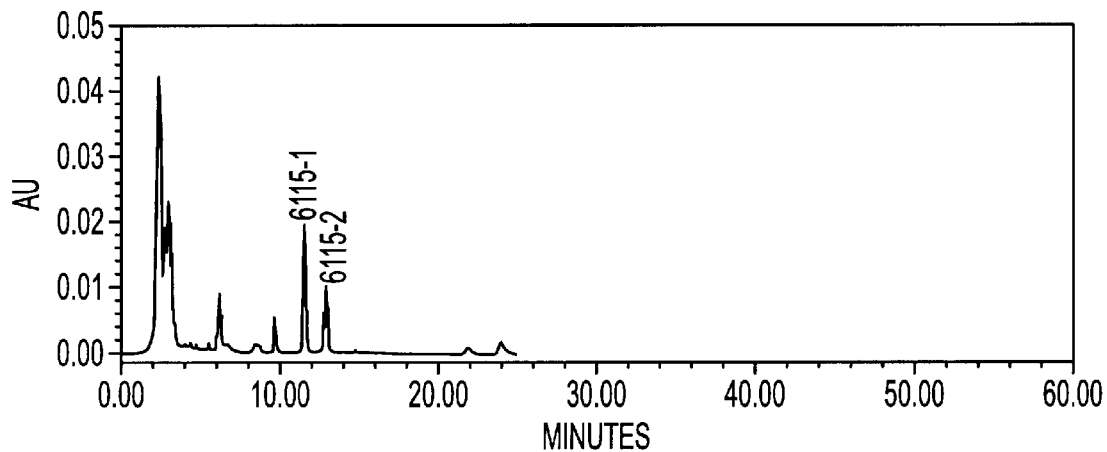
FIG. 1 shows an HPLC chromatogram of ophiopogon. Its entire chromatographic profile was detected at 214 nm wavelength using method 1 of the HPLC analysis (see infra). There were two discrete peaks, 6115-1 and 6115-2, which had a retention time of 11.5 min and 13 min, respectively, shown in the chromatogram. These two peaks could be used to identify ophiopogon.

The present invention provides six (6) pharmaceutical compositions (so-called STA-3 series [STA-31 to STA-36]). All of the compositions within this STA-3 series possess pharmaceutical effects on immunological disorders, particularly on suppression of IgE production and down regulation of the synthesis of interleukin-4 (IL-4) gene.

Antigen or allergen-mediated asthma is a respiratory disease primarily due to chronic inflammatory reaction. The inflammatory reaction is mediated by the release of inflammatory factors, such as platelet activation factor, histamine, prostaglandin, and leukotrien, from the cells. Inflammatory reaction stimulates antigenic response in T lymphocytes (T cells), particularly CD4+cells. There are two types of CD4+ cells. Th1 type of CD4+cells secrets cytokine (IFN-γ). Th2 type of CD4+cells secrets interleukin-4 (IL-4). Most of the allergic asthma patients are Th2 type. The allergen stimulates the Th2 cells to produce excess IL-4, which in turn induces the production and secretion of IgE from B lymphocytes.

The herbal contents of STA-31 to STA-36 are shown in Table 1.

TABLE 1

Herbal Compositions in the STA-3 Series

| Herbal Composition | Herb #1 | Herb #2 | Herb #3 | Herb #4 | Herb #5 |
|---|---|---|---|---|---|
| STA-31 | Ophiopogon | Pinellia | Raw Licorice | Tang-Shen | Taiwan Adenostema |
| STA-32 | Ophiopogon | Pinellia | Raw Licorice | Tang-Shen | Heartleaf Houttuynia |
| STA-33 | Ophiopogon | Pinellia | Raw Licorice | Tang-Shen | Lantern Tridax |
| STA-34 | Ophiopogon | Pinellia | Raw Licorice | American Ginseng | Taiwan Adenostema |
| STA-35 | Ophiopogon | Pinellia | Raw Licorice | American Ginseng | Heartleaf Houttuynia |
| STA-36 | Ophiopogon | Pinellia | Raw Licorice | American Ginseng | Lantern Tridax |

Among the six STA-3 compositions, STA-36 is the most preferable one.

Each of the STA-3 compositions contains five (5) herbs, in which three (3) out of 5 are essential herbs, which are ophiopogon (also known as black leek), pinellia, and raw licorice. The fourth herb can be either tang-shen or American ginseng. The fifth herb is selected from the group consisting of Taiwan adenostema, Lantern Tridax, and Heartleaf houttuynia. Taiwan adenostema and Heartleaf houttuynia, according to available herbal literatures, can only be found in Taiwan. Lantern tridax can be found in Taiwan and South America. The pharmaceutical names, botanical names, family, and major ingredients of the STA-3 compositions are shown in Table 2.

TABLE 2

Pharmaceutical/Botanical Names and Major Ingredients of the Herbs in STA-3 Pharmaceutical Composition

| Herb | Pharmaceutical Name | Botanical/ Zoological Name | Family | Major Ingredients |
|---|---|---|---|---|
| Ophiopogon (black leek) | Tuber Ophiopogonis Japonici | Ophiopogon japonicus Ker-Gawl. | Liliaceae | Ophiopogonin, Ruscogenin,β-Sitosterol, Stigmasterol |
| Tang-Shen | Radix Codonopsitis Pilosulae | Codonopsis pilosula (Franch.) Nannf. | Campanulaceae | saponins, alkaloids, taraxerylacetate, friedelin, sucrose, glucose, inulin |
| American Ginseng | Radix Panacis Quinquefolii | Panax quinquefolium L. | Araliaceae | saponins, panaquilon |
| Pinellia | Tuber Pinellia, Rhizoma Pinellia Ternatae | Pinellia ternata (Thunb.) Breitenbach | Araceae | coniine, protoanemonin, homogentisic acid, nicotine, aspartic acid, glutamic acid, arginine, β-sitosterol, cholesterol |
| Raw Licorice | Radix Glycyrrhizae Uralensis | Glycyrrhizaeuralensis Fisher or Glycyrrhiza glabra Linné. | Leguminosae | Azetidine-2-carboxylic acid, Aspartate, Homoserine, Diaminobutyric Acid, Digitalis Glycoside |

TABLE 2-continued

Pharmaceutical/Botanical Names and Major Ingredients of the Herbs in STA-3 Pharmaceutical Composition

| Herb | Pharmaceutical Name | Botanical/ Zoological Name | Family | Major Ingredients |
|---|---|---|---|---|
| Lantern Tridax | Herba Tridacis procumbentis | Tridax procumbens Linn. | Compositae | polysaccharide |
| Taiwan Adenostema | Herba Adenostemmatis | Adenostema lavenia (L.) Ktze. | Compositae | |
| Heartleaf Houttuynia | Herba Houttuyniae | Houttuynia cordata Thunberg | Saururaceae | decanoyl acetaldehyde, lauric aldehyde, methyl-n-nonylketone, myrcene, capric aldehyde, capric acid, cordarine, calcium sulfate, calcium chloride, isoquercitrin, reynoutrin, hyperin |

Ophiopogon (Radix Ophiopogonis) belongs to the family of Liliaceae. The tuber (root) of Ophiopogon has medicinal effects. The best harvesting season for ophiopogon is in the summer. After harvested, the tuber of ophiopogon should be washed clean to get rid of unwanted dirt or rootlets, which was followed by drying under sun to preserve for later use. Ophiopogon tuber is the enlarged part of the root. Ophiopogon could be found in provinces such as Zhejiang, Sichuan, and Jiangsu, of China. The aqueous extract of ophiopogon was reported by Yu et al. (1991), China Journal of Chinese Materia Medica, 16:584–585, to enhance the clearance of iv charcoal particles in mice, and antagonize the leukopenia caused by clophosphamide.

Tang-shen (Radix Codonopsitis Pilosulae) belongs to the family of Campanulaceae. The medicinal effects of Tang-Shen is in the root. Tang-shen can be either collected in the wild or cultivated. The typically harvest season for tang-shen is in autumn. After harvested, the root of tang-shen was dried under sun, and cut into segments for later use. Tang Shen could be found in Nantou Shien and Taichung Shien of Taiwan.

American ginseng (Radix Panacis Quinquefolii) belongs to the family of Araliaceae. The medicinal effects of American ginseng is in the root. American ginseng can be found in northern United States and Canada. It has also been widely cultivated in France and northern China. The best harvest season for American ginseng is in autumn.

Pinellia (Tuber Pinelliae, Rhizoma Pinellia Ternatae) belongs to the family of Araceae. The tuber (after the cork layer has been removed) of pinellia has medicinal effects. The plant grows in Sichuan, Hubei, Henan, Guizhou, and Anhui provinces of China. The normal harvest season of pinellia is between July and September. Pinellia can be found in Taichung Shien of Taiwan.

Raw licorice (Radix Glycyrrhizae Uralensis) belongs to the family of Leguminosae. The root and stolon, with (unpeeled) or without (peeled) the periderm, of raw licorice have medicinal effects. Raw licorice contains not less that 2.5% of glycyrrhizic acid ($C_{42}H_{62}O_{16}$), calculated on the basis of dried material, which can be used as chemical marker for raw licorice. Raw licorice can be found in inner Mongolia, Gansu, Xinjiang, and northeastern China. The best harvest seasons for raw licorice are either in spring or autumn. In Taiwan, raw licorice can be found in Taichung Shien. Licorice root has anti-inflammatory properties and can be used alone to help release symptoms of asthma. See H. W. Morningstar, Sentient Times: Alternative for Personal and Community Transformation (1998), 6:16–17. Licorice roots are also useful for treating bronchitis. See T. David, Miracle Medicines of the Rainforest: A Doctor's Revolutionary Work With Cancer And AIDS Patients (1997), pp. 66–79.

Lantern tridax (Herba Tridacis procumbentis) belongs to the family of Compositae. The medicinal effects of lantern tridax come from the dried whole plant. Lantern tridax can be found in Nantou Shien, Taichung Shien, and Yunlin Shien, and the city of Taichung of Taiwan. Lantern tridax has also been found in South America.

Diwan et al., Indian Journal of Physiology & Pharmacology (1983), 27: 32–36, disclose that the juice extracted from the leaves of lantern tridax has effects resembling dexamethasone on wound contraction and granulation, but significantly counteracts the effects of dexamethasone on tensile strength and epithelization. Gan et al., China Medical College Annual Bulletin (1977), 8: 526, disclose that leaves of lantern tridax is useful for diminishing inflammation, releasing symptoms of fever, and curing pneumonia and cough.

Taiwan adenostema (Herba Adenostemmatis) belongs to the family of Compositae. Taiwan adenostema usually grows near water or in wetland. The medicinal effects of Taiwan adenostema come from the entire plant, either used freshly or in dried form. The best harvest seasons are in summer or early autumn. Taiwan adenostema can be found not only in Taiwan but also in Yunnan, Guangxi, Guizhou, Jiangxi, and Chekiang provinces of China. Taiwan adenostema contains 11-hydroxylated kauranic acid.

Heartleaf houttuynia or Houttuynia Herb (Houttuyniae cum Radice Houttuyniae Cordatae) is the terrestrial part of Houttuynia cordata Thunberg. It belongs to the family of Saururaceae. Heartleaf houttuynia grows throughout the Yangtze river valley and south in China. The best harvest season is during the flowering season in late summer to early autumn. Hanhong Heartleaf houttuynia can be found in Taichung Shien of Taiwan.

In general, all STA-3 compositions are prepared as follows:
(1) All herbs except ophiopogon, which include pinellia, American ginseng (or tang-shen), raw licorice, and lantern tridax (or Taiwan adenostema, or heartleaf houttuynia), were cut, dehydrated, ground, and passed through a sieve to produce herbal powder.
(2) Ophiopogon was prepared by water extraction followed by condensation.
(3) The ophiopogon extract was mixed with the herbal powder of step (1) and granulated to form granules. The granules were packaged or encapsulated.

The following examples are illustrative, and should not be viewed as limiting the scope of the present invention. Reasonable variations, such as those occur to reasonable artisan, can be made herein without departing from the scope of the present invention.

EXAMPLE 1

Preparation of STA-3 Pharmaceutical Compositions

As indicated in Table 1 above, the STA-3 series of pharmaceutical compositions contained six (6) combinations. The quantity (by weight) of each herbs used in the combinations is illustrated in Table 3.

TABLE 3

Quantity (by Weight) of each Herbs Used In STA-3

| Exp. No. | Name | Ophio-pogon (kg) | Tang-shen, or Notoginseng, or American Ginseng (kg) | Pinel-lia (kg) | Lico-rice (kg) | Lantern tridax, or Taiwan adenostema, or Heartleaf houttuynia (kg) |
|---|---|---|---|---|---|---|
| 1 | STA-31 | 3.00 | 1.00 (Tang-shen) | 2.00 | 1.00 | 1.00 (Taiwan adenostema) |
| 2 | STA-32 | 3.00 | 1.00 (Tang-shen) | 2.00 | 1.00 | 1.00 (Heartleaf Houttuynia) |
| 3 | STA-33 | 3.00 | 1.00 (Tang-shen) | 2.00 | 1.00 | 1.00 (Lantern tridax) |
| 4 | STA-34 | 3.00 | 1.00 (American Ginseng) | 2.00 | 1.00 | 1.00 (Taiwan adenostema) |
| 5 | STA-35 | 3.00 | 1.00 (American Ginseng) | 2.00 | 1.00 | 1.00 (Heartleaf Houttuynia) |
| 6 | STA-36 | 3.00 | 1.00 (American Ginseng) | 2.00 | 1.00 | 1.00 (Lantern tridax) |

The method of preparing STA-31 to STA-36 pharmaceutical compositions primarily the same as the general method for preparing STA-3 composition (supra).
(1) All applicable herbs except ophiopogon, in the amounts as indicated in Table 3, were cut, dehydrated, ground, and passed through a sieve (preferably 40–120 mesh) to produce herbal powder.
(2) Ophiopogon in the amount as indicated in Table 3 was immersed in water in a frying-boiling container where the water volume was at least 10 cm above the top of ophiopogon. The submerged ophiopogon was heated at 97 to 103° C. for about sixty (60) minutes twice to produce an ophiopogon extract solution. Then, the ophiopogon extract solution was passed through a sieve (approximately 100 mesh). The filtrate was collected. The ophiopogon filtrate was then condensed at a temperature of 50 to 60° C. under vacuum condition with pressure between 400 and 650 mm-Hg to obtain a liquid condensate with a desirable concentration. It was preferred that the liquid condensate was about 1/14 of the ophiopogon filtrate.
(3) The liquid condensate of ophiopogon was mixed with the herbal powders of the rest of the herbs. The mixture was then transferred to the fluidized granulator and placed in a spraying tube made of filtered fabric. The granulator was set at 90 to 110° C. After pre-heating for about five (5) minutes, the mixture was sprayed at about 40 to 55 seconds per time for an appropriate amount of times and the spraying tube was patted at a frequency of once in every 10 seconds. After granulation, the granules were dried and then cooled off. The granules were passed through sieves and packaged in PE bags. The preferred water content of the granules was less than 6%. The granules can be further encapsulated in any of the conventional capsules, including, but not limited to, natural gelatin, pectin, casein, collagen, protein, modified starch, and polyvinyl pyrrolidone.

EXAMPLE 2

Quality Controls of the STA-3 Pharmaceutical Compositions Using High Performance Liquid Chromatography (HPLC)

The present invention used HPLC techniques to ensure the quality of the herbs was well under control. Three HPLC methods were developed to accommodate the chemical and physiological characteristics of each herb. The three HPLC methods were described as follows:

(A) Method 1 of the HPLC Analysis

Method 1 used a precolumn Lichrospher RP-18 endcapped (5 $\mu$m, 4.0 ID×10 mm, Merck), and a Cosmosil 5C18-MS column (5 $\mu$m, Nacalai tesque 5C18-MS, 4.6 ID×250 mm) at room temperature. The mobile phase of the column was a gradient containing (A) $H_2O:KH_2PO_4$:10% $H_3PO_4$ (1000 ml:2.72 g:1 ml, v/w/v), (B) $CH_3CN$, (C) $H_2O$, and (D) $CH_3OH$. The elution gradient was described in Table 4. The flow rate was 1.0 ml/min. The detection wavelength was 250 nm. The total retention time of the analysis was 60 minutes.

TABLE 4

Mobile Phase Gradient of Method 1

| Time | (A) | (B) | (C) | (D) |
|---|---|---|---|---|
| Initial | 90 | 10 | 0 | 0 |
| 30 | 75 | 25 | 0 | 0 |
| 40 | 65 | 35 | 0 | 0 |
| 55 | 0 | 75 | 25 | 0 |
| 60 | 0 | 10 | 90 | 0 |

Post Run: 15 min.

(B) Method 2 of the HPLC Analysis

Method 2 of the HPLC analysis used a precolumn Lichrospher RP-18 endcapped (5 $\mu$m, 4.0 ID×10 mm, Merck), and a Cosmosil 5C18-MS column (5 $\mu$m, Nacalai tesque 5C18-MS, 4.6 ID×250 mm) at 35° C. The mobile phase of the column was a gradient containing (A) 10 mM $KH_2PO_4$+10 mM $K_2HPO_4$+ 0.01% $H_3PO_4$ ($KH_2PO_4$:$K_2HPO_4$:10% $H_3PO_4$:$H_2O$=1.36 g:1.74 g:1 ml:1000 ml), (B) $CH_3CN$, (C) $H_2O$, and (D) $CH_3OH$. The elution gradient was described in Table 5. The flow rate was 1.0 ml/min. The detection wavelength was 260 nm. The total retention time of the analysis was 60 minutes.

TABLE 5

Mobile Phase Gradient of Method 2

| Time (min) | (A) | (B) | (C) | (D) |
|---|---|---|---|---|
| Initial | 100 | 0 | 0 | 0 |
| 25 | 60 | 0 | 20 | 20 |
| 30 | 20 | 0 | 20 | 60 |
| 35 | 100 | 0 | 0 | 0 |

Post run: 15 min.

(C) Method 3 of the HPLC Analysis

Method 3 of the HPLC analysis used a precolumn Lichrospher RP-18 endcapped (5 μm, 4.0 ID×10 mm, Merck), and a Cosmosil 5C18-MS column (5 μm, Nacalai tesque 5C18-MS, 4.6 ID×250 mm) at 35° C. The mobile phase of the column was a gradient containing (A) $H_2O:KH_2PO_4$ (1000 ml:2.72 g, v/w), (B) $CH_3CN$, (C) $H_2O$, and (D) $CH_3OH$. The elution gradient was described in Table 6. The flow rate was 1.0 ml/min. The detection wavelength was 203 nm. The total retention time of the analysis was 60 minutes.

TABLE 6

Mobile Phase Gradient of Method 3

| Time (min) | (A) | (B) | (C) | (D) |
|---|---|---|---|---|
| Initial | 80 | 20 | 0 | 0 |
| 40 | 65 | 35 | 0 | 0 |
| 55 | 0 | 80 | 20 | 0 |
| 60 | 0 | 20 | 80 | 0 |

Post run: 15 min.

EXAMPLE 3
HPLC Analysis of the Herbs Used in STA-3 Compositions

The HPLC analysis of the herbs used in STA-3 composition, which includes the method, major marker(s), and detection wavelength of each herb, are summarized in Table 7. The HPLC chromatograms of the STA-36 herbs are shown in FIGS. 1–5.

TABLE 7

HPLC Analysis of Herbs Used in STA-36

| Herbal Name | HPLC Analytical Method | Marker(s) | Retention Time (min) | Wavelength (nm) |
|---|---|---|---|---|
| Ophiopogon | Method 1 | 6115-1 | 11.5 | 214 |
|  |  | 6115-2 | 13.0 | 214 |
| Pinellia | Method 2 | Adenine | 14.8 | 250 |
|  |  | Guanosine | 17.0 | 250 |
| Raw Licorice | Method 1 | Glycyrrhizin | 46.4 | 250 |
| American Ginseng | Method 3 | Ginsenoside $Rb_1$ | 37.5 | 203 |
| Lantern Tridax | Method 1 | FY-1 | 28.0 | 250 |
|  |  | FY-2 | 31.6 | 250 |
|  |  | FY-3 | 33.5 | 250 |
|  |  | FY-4 | 18.3 | 250 |

Before HPLC analysis, 0.5 g of the herbal sample was mixed with 20 ml solution containing 70% of methanol. The sample solution was sonicated for 15 min at room temperature and placed in a rotating water bath at 40° C. for 20 min with the rotation speed set at 160 rpm. The sample solution was then left to sit for about 30 min to allow the debris to precipitate. Ten (10) ml of the supernatant was then pipetted out and passed through a 0.45 μm filter. The filtrate was ready for HPLC analysis. Twenty (20) μl of the filtrate was taken for HPLC analysis.

Results

The HPLC chromatogram of ophiopogon is shown in FIG. 1. As shown in Table 7, method 1 of the HPLC analysis was used to detect ophiopogon at 214 nm wavelength. Two distinctive peaks, 6115-1 and 6115-2, were identified on the ophiopogon HPLC chromatogram. 6115-1 had a retention time of 11.5 min. 6115-2 had a retention time of 13 min. Although the chemical components in these two peaks were not yet identified, they could be used for the purpose of ensuring the quality of ophiopogon.

Figure 2:
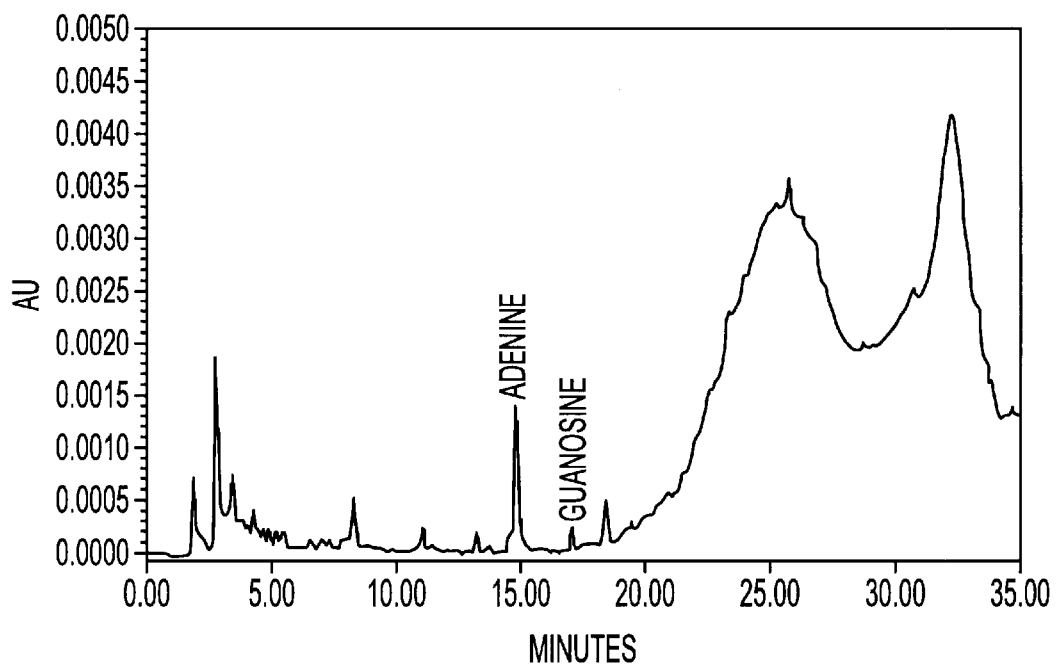
FIG. 2 shows an HPLC chromatogram of pinellia. Two chemical markers, adenine and guanosine, were detected at 260 nm wavelength using method 2 of the HPLC analysis. Adenine has a retention time of 14.8 min. Guanosine has a retention time of 17 min.

The HPLC chromatogram of pinellia is shown in FIG. 2. As shown in Table 7, using method 2 of the HPLC analysis to detect pinellia at 250 nm wavelength, pinellia had shown two distinctive chemical markers, i.e., adenine and guanosine, both are constituents of nucleic acids. Adenine also has effect of elevating serum aldolase. Adenine had a retention time of 14.8 min. Guanosine had a retention time of 17 min.

Figure 3:
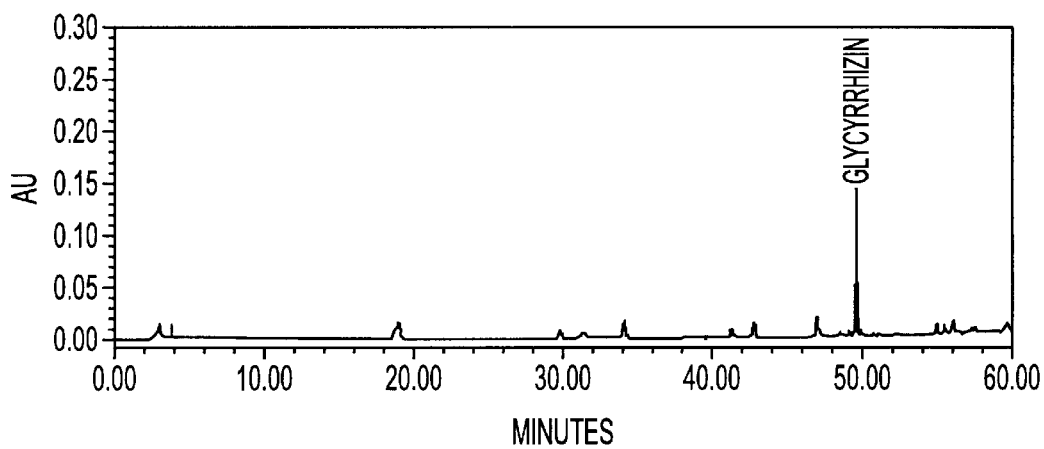
FIG. 3 shows an HPLC chromatogram of raw Licorice. A chemical marker, glycyrrhizin (Gly), was detected at 250 nm wavelength using method 1 of the HPLC analysis. Gly has a retention time of 46.4 min.

The HPLC chromatogram of raw licorice is shown in FIG. 3. As shown in Table 7, using method 1 of the HPLC analysis to detect raw licorice at 250 nm wavelength, a chemical marker "glycyrrhizin" was found in the raw licorice HPLC chromatogram. Glycyrrhizin ($C_{42}H_{62}O_{16}$) is a very sweet substance. It is known to have detoxification, anti-inflammation, and haemolysis effects, and has been used to treat Addison's disease. The retention time for glycyrrhizin is 46.4 min.

Figure 4:
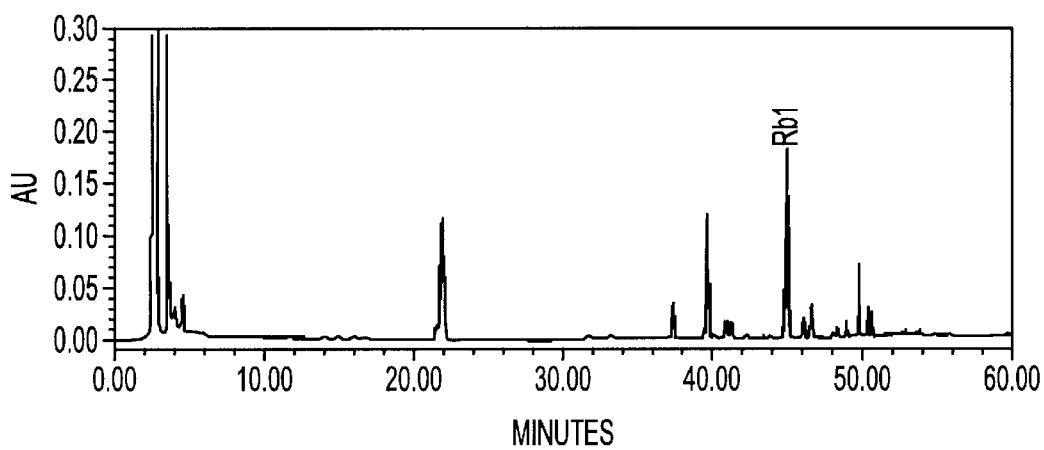
FIG. 4 shows an HPLC chromatogram of American Ginseng. A chemical marker, ginsenoside $Rb_1$ ($Rb_1$), was detected at 203 nm wavelength using Method 3 of the HPLC analysis. $Rb_1$ has a retention time of 37.5 min.

The HPLC chromatogram of American ginseng is shown in FIG. 4. As shown in Table 7, using method 3 to detect American ginseng at 203 nm wavelength, a chemical marker "ginsenoside $Rb_1$" was found in the American ginseng HPLC chromatogram. Ginsenoside $Rb_1$ has medicinal effects on dilating blood vessel, relieving fatigue, and avoiding haemolysis.

Figure 5:
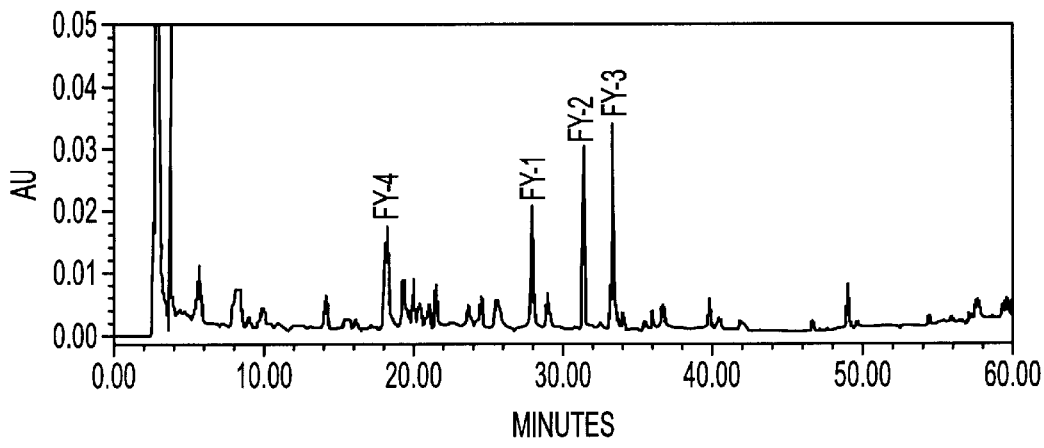
FIG. 5 shows an HPLC chromatogram of Lantern Tridax. There were four (4) distinctive peaks, FY-1 to FY-4, detected at 250.0 nm wavelength using method 2 of the HPLC analysis. FY-1 has a retention time of 28 min. FY-2 has a retention time of 31.6 min. FY-3 has a retention time of 33.5 min. FY-4 has a retention time of 18.3 min.

The HPLC chromatogram of lantern tridax is shown in FIG. 5. As indicated in Table 7, using method 1 of the HPLC analysis to detect lantern tridax at 250 nm wavelength, four (4) distinctive peaks, FY-1 to FY-4, were identified. FY-1 had a retention time of 28.0 min. FY-2 had a retention time of 31.6 min. FY-3 had a retention time of 33.5 min. FY-4 had a retention time of 18.3 min. Due to the consistent appearance of these four peaks, even though the chemical contents associated with these four peaks were still not yet identified, they could be used for the purpose of identifying and ensuring the quality of lantern tridax.

EXAMPLE 4
Thin-Layer Chromatography (TLC) Characterization of Raw Licorice, Ophiopogon, Pinellia, and Lantern Tridax In addition to HPLC, some of the herbs used in the STA-36 compositions, including raw licorice, ophiopogon, pinellia, and lantern tridax, can be characterized by thin-layer chromatography (TLC) methods.

The TLC method used a stationary phase of silica gel 60 F254 (which was bound to the TLC plate) and three mobile phase (or dissociation) solvents, depending upon the characteristics of the herbs. The first solvent contained ethyl acetate, 4 N ammonia water, and ethanol in a volume ratio of 4:1:2 (v/v/v). This first solvent was particularly useful for characterizing raw licorice. The second solvent contained butanol, 4 N ammonia water, and ethanol in a volume ratio of 5:2:1 (v/v/v). This second solvent was particularly useful for characterizing ophiopogon and American ginseng. The third solvent contained chloroform ($CHCl_3$) and methanol at a volume ratio of 5:1 (v/v). This third solvent was particularly useful for characterizing lantern tridax. For each TLC determination, 5 μl of sample was added at the starting point of the TLC plate. The plate was placed in a TLC chamber within which the mobile phase solvent was applied. The solvent was allowed to migrate up to 9 cm. The results of the TLC determination were described as follows:

(A) Raw Licorice

Raw licorice was analyzed by TLC using a stationary phase of silica gel 60 F254 attaching to a TLC plate, and a mobile phase solvent containing ethyl acetate:4N ammonia water:Ethanol=4:1:2 (v/v/v). After the application of the sample, the TLC plate was placed into the TLC chamber which contained the mobile phase solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A yellow spot which represented raw licorice appeared on the plate at approximately Rf=0.5. Rf=(the distance [cm] between the spot and the sample application point)/total migration distance [i.e., 9 cm]).

(B) Ophiopogon

Ophiopogon was analyzed by TLC using a stationary phase of Silica gel 60 F254 attaching to a TLC plate and a mobile phase solvent containing butanol:4N ammonia water:ethanol=5:2:1 (v/v/v). After the application of the sample, the TLC plate was placed into the TLC chamber which contained the mobile phase solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A brown spot which represented ophiopogon appeared on the plate at approximately Rf=0.4.

(C) American Ginseng

American ginseng was analyzed by TLC using a stationary phase of Silica gel 60 F254 attaching to a TLC plate and a mobile phase solvent containing butanol:4N ammonia water:ethanol=5:2:1 (v/v/v). After the application of the sample, the TLC plate was placed into the TLC chamber which contained the mobile phase solvent with the upper liquid mark not to exceed the sample application point. The solvent was allowed to migrate up to 9 cm from the sample application point. Then, the TLC plate was taken out of the TLC chamber and air dried. The dried TLC plate was sprayed with a spraying reagent containing vanillin/$H_2SO_4$. The plate was then activated under heat at 105° C. for two (2) minuets. A purplish spot which represented American ginseng appeared on the plate at approximately Rf=0.3.

(D) Lantern Tridax

Lantern tridax was analyzed by TLC using a stationary phase of Silica gel 60 F254 attaching to a TLC plate and a mobile phase solvent containing chloroform:methanol=5:1 (v/v). After the application of the sample, the TLC plate was placed into the TLC chamber which contained the mobile phase solvent with the upper liquid mark not to exceed the sample application point. The solvent was allowed to migrate up to 9 cm from the sample application point. Then, the TLC plate was taken out of the TLC chamber and air dried. The dried TLC plate was placed under a UV detector and detected at 366 nm wavelength. A pale yellow fluorescent spot which represented lantern tridax appeared on the plate at approximately Rf=0.3.

EXAMPLE 5
Effects of Five Traditional Chinese Herbal Decoction Formulations on Allergen-Induced IgG, IgE, and IL-4 in Mice The effects of five (5) traditional Chinese herbal decoction formulations on suppression of allergen-induced immunoglobulin G (IgG), immunoglobulin E (IgE) synthesis, and expression of interleukin-4 (IL-4) gene were investigated using BALB/c mice sensitized with D.P. (*Dermatophagoides pteronyssimus*) allergen "Der p 5". *Dermatophagoides pteronyssimus* is the house dust mite which acts as an antigen and produces an allergic asthmatic reaction in atopic person.

The formulations of these 5 traditional Chinese decoction groups are shown in Table 8. These 5 traditional Chinese decoction groups are known to have special effects on treating patients with lung-related ailments, such as asthma.

TABLE 8

Formulations of Five Traditional Chinese Herbal Decoctions

| Name of Traditional Chinese Herbal Decoctions | Herbal Ingredients (with weight ratio) |
|---|---|
| White-Draining Powder | licorice (2.25), bark of mulberry root (4.5), cortex of wolfberry root (4.5), polished round-grained nonglutinous rice/japonica rice (6). |
| Little Green-Blue Dragon Decoction | pinellia (4), ephedra (4), Chinese herbaceous peony (4), Chinese wild ginger (1.5), licorice (4), dried ginger (4), cinnamon twig (4), schisandra fruit (1.5). |
| Ophiopogon Decoction | ginseng (2), polished round-grained nonglutinous rice/japonica rice (4), pinellia (2), Chinese date/jujube (2), licorice (2), ophiopogon (8). |
| Dryness-Clearing Lung-Rescuing Decoction | white mulberry leaf (7.5), ass-hide glue/gelatin (2), ginseng (2), gypsum (6.5), licorice (2.5), ophiopogon (3), apricot seed/kernel (2), black sesame seeds (2.5), loquat leaf(2). |
| Perilla Fruit Qi-Downbearing Decoction | purple perilla fruit (5), tangerine peel (3), pinellia (5), Chinese angelica root (2), hogfennel root (2), licorice (2), cinnamon bark (3), magnolia bark (2), fresh ginger rhizome (2), Chinese date/jujube (1). |

Experimental Design (A) Preparation of Herbal Materials

Fifty (50) mg of each of the above indicated herbal formulations (all from Sun Ten Sci. Pharm. Corp., Taipei, Taiwan) were mixed with 180 μl of Tween 80, respectively, and homogenized (homogenizer DC-3S, Xinguang Precision Instrument Industrial Limited, Inc., Taiwan). Water was added to the homogenate to bring the final volume to 2 ml, and the final concentration 25 mg/ml. Each mouse received 0.4 ml/per 20 g body weight of one of the herbal composition solution or placebo every other day for fourteen (14) days.

(B) Animals

Female BALB/c mice aged between 4 and 6 weeks, were obtained from the animal-breeding center of the National Chung-Gong University. Mice were age- and sex-matched for each experiment.

(C) Allergen Derp5 (Dermatophagoidespteronyssinus group 5 allergen) Purification pGEX-2T plasmid was used to express Der p 5-glutathion S-transferase (GST) in *E. coli*. The molecular weight of the fusion protein was about 42 kD. The protein was purified by glutathione-conjugated agarose gel column chromatography. A single colony of the Der p 5-GST positive-bacterial strain was selected by growing the transfected *E. coli* on LB broth containing Ampicillin (100 μg/ml). The Der p 5-GST positive *E. coli* colony was further cultured to produce substantial amount of Der p 5-GST. Then, the bacterial culture was collected and centrifuged. The supernatant was discarded, and the pellet was washed with TBS (pH 7.5) and collected in a centrifuge tube. Immediately following the TBS wash, 0.1 M phenylmethylsulfonyl fluoride was added to the pellet, followed by the addition of DNase I, Tween 20, and lysozyme. The pellet was lyzed by the freeze-and-thaw process to release Der p 5+GST protein. Subsequently, EDTA was added to the cell lysate, which was then centrifuged. The pellet was discarded, and the supernatant was poured onto a glutathione-conjugated agarose gel adsorption column where Der p 5-GST protein was adsorbed onto the column. The column was washed first by TBS buffer solution at 4° C., and then by reduced glutathione in Tris-base (pH 8.0) to separate the Der p 5-GST from the agarose gel column. The purity of the Der p 5-GST protein was confirmed by SDS-PAGE. The quantity of the protein was measured by conventional protein analytical methods.

(D) Animal Sensitization

BALB/c mice were initially intraperitoneally sensitized with 10 µg of *Dermatophagoides pteronyssinus* group 5 ("Der p 5") allergen and 4 mg of aluminium hydroxide (Wyeth Pharmaceuticals, Punchbowl, Australia). Seven (7) days after the first sensitization, mice, except the placebo control group, were fed with Chinese herbal decoctions.

Three (3) weeks after the first sensitization, mice were boosted with Der p 5 again. Three (3) days after the second booster injection, mice were placed in a round plastic container where the mice were further challenged by 0.1% Der p 5 spray.

Each time after the booster injection, 50 µl of blood were collected from the tail vein of each mouse in the following day. The blood was allowed to sit at room temperature for 1 hour and then centrifuged. The serum was collected and stored at −80° C. for ELISA (see below) analysis.

(E) Determination of Der p 5-specific IgG and IgE

The amount of Der p 5-specific IgG and IgE were determined by Enzyme Linked Immunosorbent Assay (ELISA). Protein high binding plates were coated with 100 µl purified Der p 5 diluted in coating buffer (0.1 M NaHCO$_3$, pH 8.2) to a concentration of 5 µg/ml. After overnight incubation at 4° C., plates were washed three times and blocked with 3% (wt/vol) BSA-PBS buffer for 2 hr at 25° C. Sera were used at 1:100 dilution for IgG measurement and 1:10 dilution for IgE measurement in duplicate. After overnight incubation at 4° C., either biotin-conjugated monoclonal rat anti-mouse IgE mAb, or rat anti-mouse IgG mAb diluted in 0.05% gelatin buffer, was added for an additional hour. Avidin-alkaline phosphatase (1:1000) was then added and incubated for 1 hour at 25° C., followed by six (6) washes. The color reaction was developed with the addition of phosphatase substrate p-nitrophenyl phosphate, disodium. Plates were read in a microplate autoreader (Metertech, Taiwan) at 405 nm. Readings were referenced to commercial isotypes standards which were mouse anti-TNP mAb, IgG1 (107.3), IgG2a (G155-178), and IgE (IgE-3).

(F) Expression of IL-4 gene in splenocytes by RT-PCR (Reverse Transcriptase-Polymerase Chain Reaction)

The splenocytes were isolated from BALB/c mice after the animals were sensitized and challenged with Der p 5 allergen followed by treatment, respectively, of five herbal decoctions as listed in Table 8 or placebo. The splenocytes were incubated with Der p 5 (15 µg/ml) for 4 hours. RNA was extracted using Tridzol reagent (Gibco BRL, Life Technologies, U.S.A). The extracted RNA was used for the production of cDNA using Ready to go T-Primed First-Strand Kit (Pharmacia Biotch, USA). The cDNA was used as template for polymerase chain reaction (PCR). A pair of IL-4 specific primers having the sequences of:

5'-GAATGTACCAGGAGCCATATC-3' (SEQ ID NO:1); and

5'-CTCAGTACTACGAGTAATCCA-3' (SEQ ID NO:2);

was used for PCR amplification and detection of IL-4 gene. A pair of HPRT (hypoxanthine-guanine phosphoribosyltransferase) specific primers having the sequences of:

5'-GTTGGATACAGGCCAGACTTTGTTG-3' (SEQ ID NO:3); and

5'-GATTCAACTTGCGCTCATCTTAGGC-3' (SEQ ID NO:4);

was used for PCR amplification and detection of HPRT. The PCR was performed under the following conditions: 95° C. denaturation for 5 minutes, followed by 35 cycles of 95° C. for 1 minute, 72° C. for 1 minute, and 55° C. for 3 minutes in a Thermo-cycler. The PCR products were then electrophorized on a 2% agarose gel.

(G) Statistical Analysis

To assess changes of Der p 5-specific IgG, IgE, and IL-4/HPRT ratio after Der p 5 challenge, repeated measures for ANOVA were performed to compare the differences among groups. Following analysis of variance, Duncan multiple range test was used to differentiate differences between experimental and control groups. A $p<0.05$ was used to indicate statistical significant difference.

Results

Figure 6:
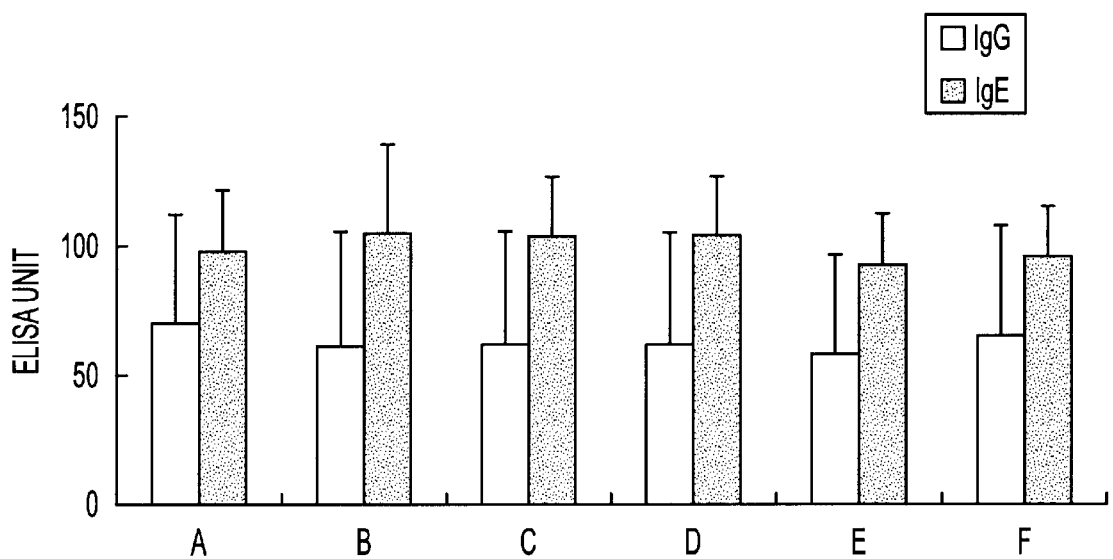
FIG. 6 shows the levels of Der p 5 (*Dermatophagoides pteronyssimus* allergen 5) specific IgG and IgE antibodies after Der p 5 inhalation challenge followed by treatment of 5 (A–F) decoction groups. The serum IgG and IgE levels were measured by ELISA. Values are Means±SEM with bar indicating the SEM. A: White-Draining Powder Group; B: Green-Blue Dragon Decoction Group; C: Ophiopogon Decoction Group; D: Dryness-Clearing lung-Rescuing Decoction Group; E: Perilla Fruit Qi-Downbearing Decoction Group; and F: Placebo Group.

As shown in FIG. 6, the levels of IgG and IgE in mice after Der p 5 challenge followed by treatment of the five traditional Chinese herbal decoctions were not significantly different from the control (placebo) group. The ELISA units for IgG in White-Draining Powder Group (A), Green-Blue Dragon Decoction Group (B), Ophiopogon Decoction Group (C), Dryness-Clearing Lung-Rescuing Decoction Group (D), Perilla Fruit Qi-Downbearing Decoction Group (E), and Placebo Group (F) were 70.9±42, 62.5±44, 63.3±44, 63.3±43, 59.7±38, and 67.4±42, respectively. The ELISA units for IgE in White-Draining Powder Group (A), Green-Blue Dragon Decoction Group (B), Ophiopogon Decoction Group (C), Dryness-Clearing Lung-Rescuing Decoction Group (D), Perilla Fruit Qi-Downbearing Decoction Group (E), and Placebo Group (F) were 99.3±23, 106.3±34, 104.9±23, 105.7±23, 93.9±21, and 97.8±19, respectively.

The results of FIG. 6 demonstrate that the five traditional Chinese herbal decoctions did not suppress the production of IgE.

Figure 7:
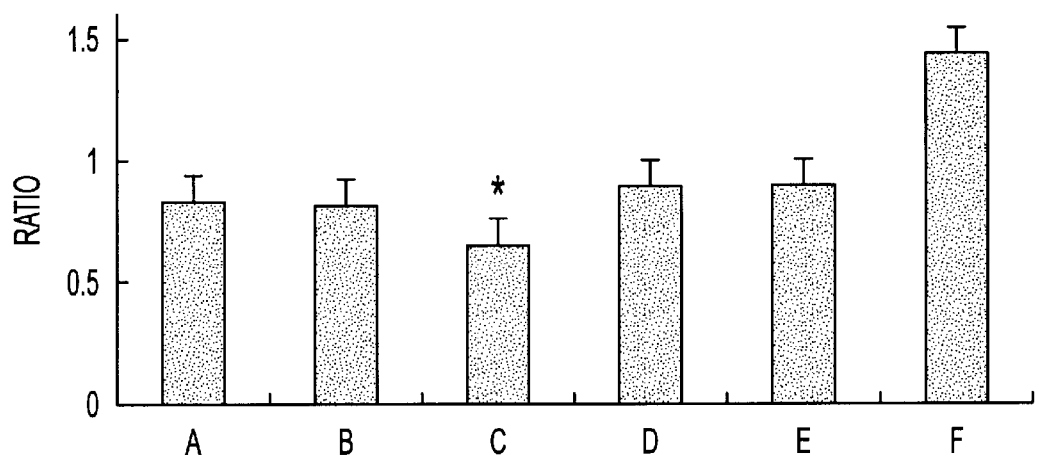
FIG. 7 shows the expression of IL-4 gene in splenocytes after Der p 5 inhalation challenge followed by treatment of 5 (A–F) decoction groups. The expression of IL-4 gene was determined by RT-PCR (reverse transcriptase-polymerase chain reaction). Values are Means±SEM with bar indicating the SEM. A: White-Draining Powder Group; B: Green-Blue Dragon Decoction Group; C: Ophiopogon Decoction Group; D: Dryness-Clearing lung-Rescuing Decoction Group; E: Perilla Fruit Qi-Downbearing Decoction Group; and F: Placebo Group. *Indicates $p<0.05$.

As shown in FIG. 7, except for ophiopogon decoction which shows a significant decrease in IL-4/HPRT, the rest of the traditional Chinese herbal decoctions have no effect with respect to the suppression of IL-4 gene production.

EXAMPLE 6

Effects of Individual Herbs in the STA-3 Series as Well as the STA-36 on Allergen-Induced IgG, IgE, and IL-4 in Mice The effects of individual herb, including ophiopogon, pinellia, raw licorice, and tang-shen, and the STA-36 on allergen-induced IgG, IgE, and IL-4 were investigated using BALN/c mice sensitized with D.P. allergen "Der p 5". The experimental designs of this example were the same as those described in Example 5 (supra).

Results

Figure 8:
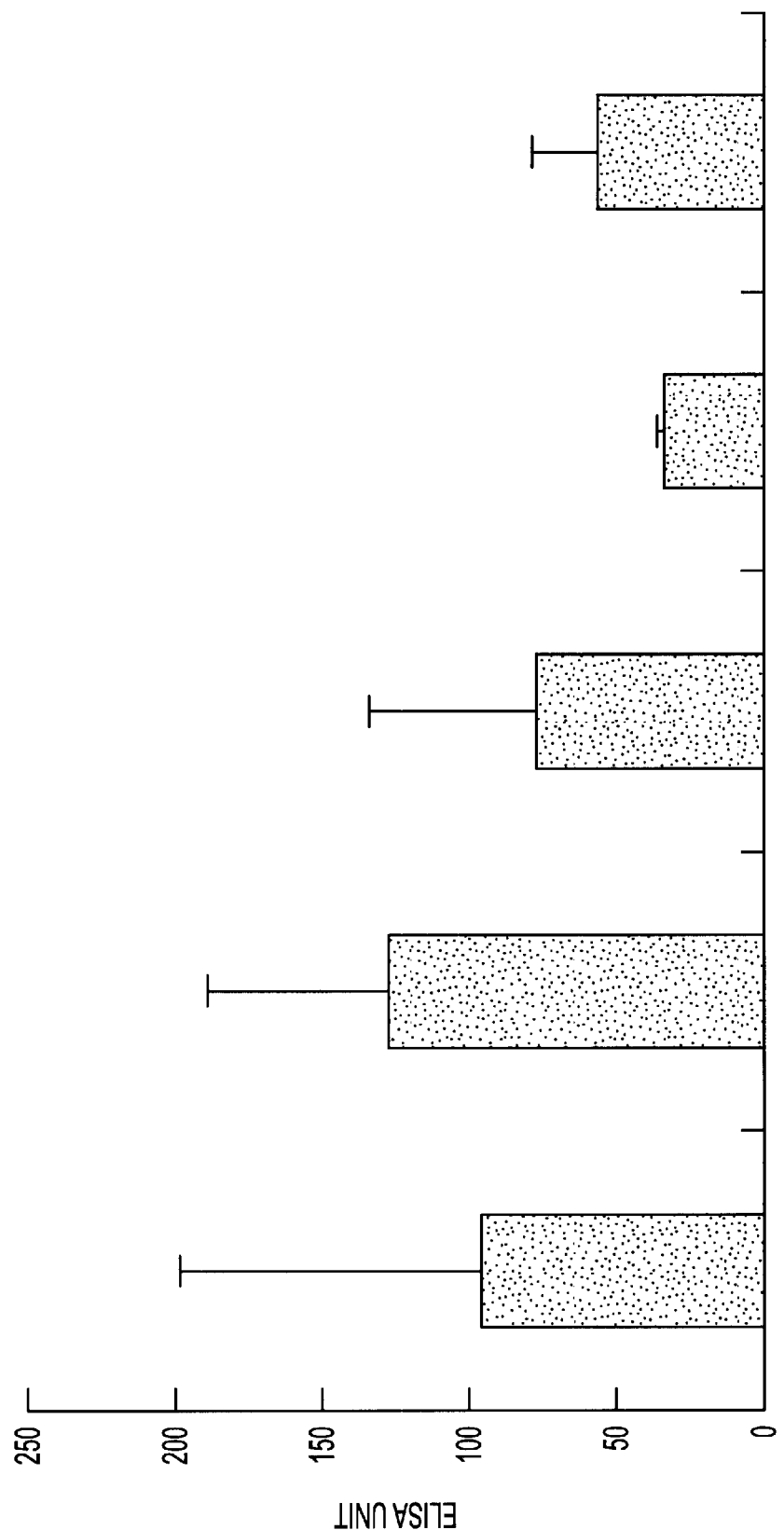
FIG. 8 shows mice serum IgG levels after challenged by allergen Der p 5 (*Dermatophagoides pteronyssimus* allergen 5) and treated with individual herb. Lane 1 shows the effect of ophiopogon treatment. Lane 2 shows the effect of tang-shen treatment. Lane 3 shows the effect of pinellia treatment. Lane 4 shows the effect of raw licorice treatment. Lane 5 is the placebo treatment. The serum IgG levels were measured by ELISA. Values are Means±SEM with bar indicating the SEM.

The IgG levels in mice serum after challenged by allergen Der p 5 and then treated by ophiopogon, tang-shen, pinellia, and raw licorice are shown in FIG. 8. The results indicated that the IgG levels were not significantly different between ophiopogon, tang-shen and pinellia treatment and placebo. The IgG level after raw licorice treatment was significantly lower than that of placebo treatment.

Figure 9:
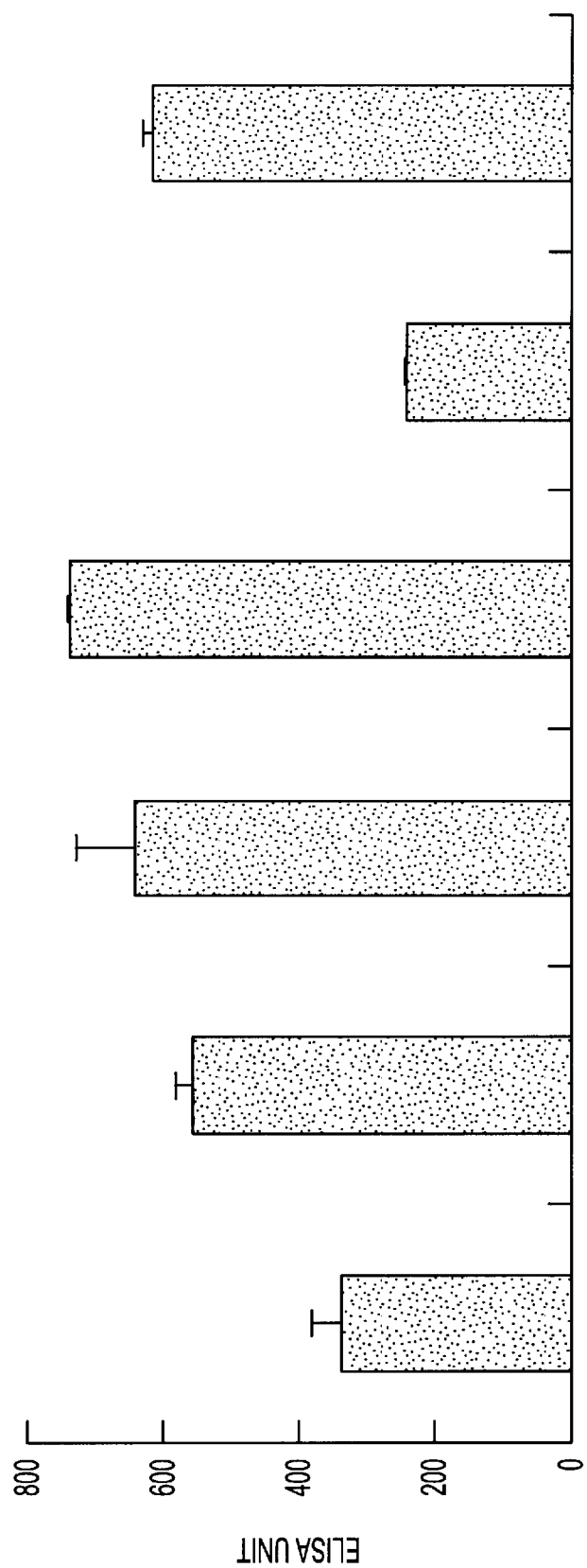
FIG. 9 shows mice serum IgE levels after challenged by Der p 5 (*Dermatophagoides pteronyssimus* allergen 5) and treated with individual herb or the pharmaceutical composition (i.e., STA-36, infra). Lane 1 shows the effect of ophiopogon treatment. Lane 2 shows the effect of tang-shen treatment. Lane 3 shows the effect of pinellia treatment. Lane 4 shows the effect of raw licorice treatment. Lane 5 shows the effect of STA-36 treatment. Lane 6 is the placebo treatment. The serum IgG levels were measured by ELISA. Values are Means±SEM with bar indicating the SEM.

However, as shown in FIG. 9, the IgE levels in mice serum after challenged by Der p 5 and then treated by ophiopogon, tang-shen, and the STA-36 composition were significantly lower than that of the placebo. In fact, after treatment with the STA-36 composition, the level of IgE was reduced by more than 2.5 times. The IgE levels after treatment of pinellia and raw licorice were insignificantly different from that of the placebo treatment.

Figure 10:
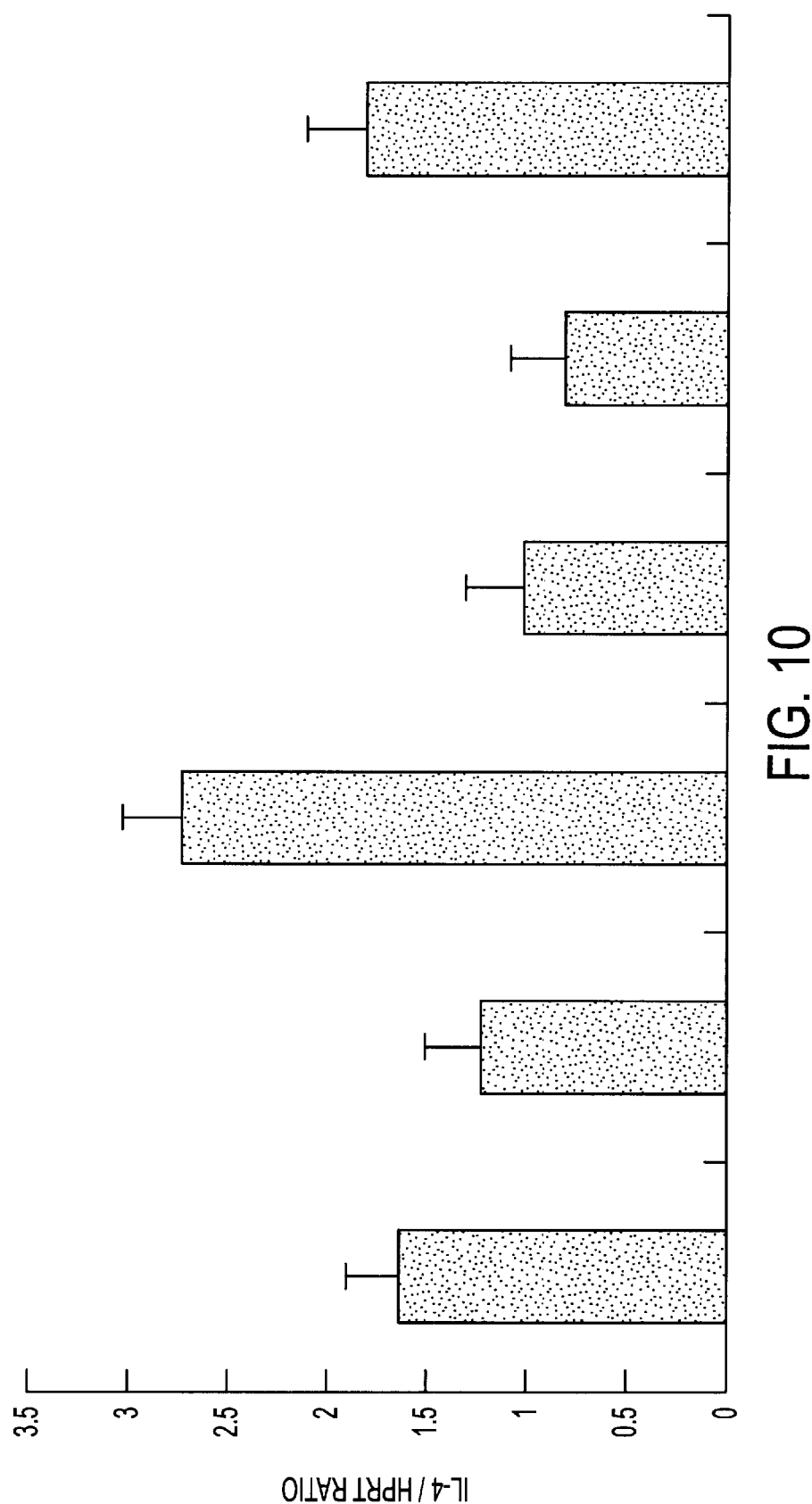
FIG. 10 shows the expression of IL-4 gene in mice splenocytes after challenged by Der p 5 (*Dermatophagoides pteronyssimus* allergen 5) and treated with individual herb or the pharmaceutical composition (i.e., STA-36, infra). The expression of IL-4 gene was determined by RT-PCR (reverse transcriptase-polymerase chain reaction). Lane 1 shows the effect of ophiopogon treatment. Lane 2 shows the effect of tang-shen treatment. Lane 3 shows the effect of pinellia treatment. Lane 4 shows the effect of raw licorice treatment. Lane 5 shows the effect of STA-36 treatment. Lane 6 is the placebo treatment.

As shown in FIG. 10, the expressions of IL-4 gene (measured by RT-PCR and expressed as IL-4/HPRT ratio) in mice splenocytes after challenged by Der p 5 and then treated by ophiopogon, tang-shen, pinellia, and raw licorice, respectively, were not significantly different from that of the placebo. However, the expression of IL-4 gene ratio) after treatment of STA-36 was significantly lower than that of the placebo, indicating that the STA-36 could down-regulate the expression of IL-4 gene.

Having described the invention in detail and by reference to the preferred embodiments it will be apparent to those skilled in the art that modifications and variations are possible without departing from the scope of the invention as defined in the following appended claims.

We claim:

1. A pharmaceutical composition for treating immunological disorder comprising an effective amount of:
   an aqueous extract of *Tuber ophiopogonis;*
   powder of *Tuber pinelliae;*
   powder of *Radix glycyrrhizae;* and powder of an herb which is one selected from the group consisting of *Herba tridacis procumbentis, Herba adenostemmatis,* and *Herba houttuyniae.*

2. The pharmaceutical composition according to claim 1, wherein said *Tuber Ophiopogonis,* said *Tuber Pinelliae,* and said *Radix Glycyrrhizae* are at a weight ratio of 3:2:1.

3. The pharmaceutical composition according to claim 1, further comprising *Radix Codonopsitis.*

4. The pharmaceutical composition according to claim 3, wherein said *Tuber Ophiopogonis,* said *Tuber Pinelliae,* said *Radix Glycyrrhizae,* said *Radix Codonopsitis,* and said *Herba Tridacis procumbentis* are at a weight ratio of 3:2:1:1:1.

5. The pharmaceutical composition according to claim 3, wherein said *Tuber Ophiopogonis,* said *Tuber Pinelliae,* said *Radix Glycyrrhizae,* said *Radix Codonopsitis,* and said *Herba Adenostemmatis* are at a weight ratio of 3:2:1:1:1.

6. The pharmaceutical composition according to claim 3, wherein said *Tuber Ophiopogonis,* said *Tuber Pinelliae,* said *Radix Glycyrrhizae,* said *Radix Codonopsitis,* and said *Herba Houttuyniae* are at a weight ratio of 3:2:1:1:1.

7. The pharmaceutical composition according to claim 1, further comprising *Radix Pancis Quinquefolii.*

8. The pharmaceutical composition according to claim 7, wherein said *Tuber Ophiopogonis,* said *Tuber Pinelliae,* said *Radix Glycyrrhizae,* said *Radix Pancis Quinquefolii,* and said *Herba Tridacis procumbentis* are at a weight ratio of 3:2:1:1:1.

9. The pharmaceutical composition according to claim 7, wherein *Tuber Ophiopogonis, Tuber Pinelliae, Radix Glycyrrhizae, Radix Pancis Quinqujefolii,* and Taiwan adenostema are at a weight ratio of 3:2:1:1:1.

10. The pharmaceutical composition according to claim 7, wherein *Tuber Ophiopogonis, Tuber Pinelliae, Radix Glycyrrhizae, Radix Codonopsitsis,* and heartleaf houttuynia are at a weight ratio of 3:2:1:1:1.

11. A method for preparing the pharmaceutical composition according to claim 4, comprising:

grinding *Tuber Pinelliae, Radix Glycyrrhizae, Radix Codonopsitsis,* and one of *Herba Tridacis procumbentis,* Taiwan adenostema, and Heartleaf Houttuynia into herbal powder;

boiling *Tuber Ophiopogonis* in water to extract pharmaceutical ingredients from *Tuber Ophiopogonis;* mixing said herbal powder with said pharmaceutical ingredients from *Tuber Ophiopogonis* to form a herbal mixture.

12. The method according to claim 11, wherein said herbal mixture is granulated.

13. The method according to claim 12, wherein said granulated herbal mixture is encapsulated.

14. A method for preparing the pharmaceutical composition according to claim 8, comprising:

grinding *Tuber Pinelliae, Radix Glycyrrhizae, Radix Pancis Quinqujefolii,* and one of *Herba Tridacis procumbentis,* Taiwan adensotema, and Heartleaf Houttuynia into herbal powder;

boiling *Tuber Ophiopogonis* in water to extract pharmaceutical ingredients from *Tuber Ophiopogonis* mixing said herbal powder with said pharmaceutical ingredients from *Tuber Ophiopogonis* to form a herbal mixture.

15. The method according to claim 14, wherein said herbal mixture is granulated.

16. The method according to claim 15, wherein said granulated herbal mixture is encapsulated.

17. A method of treating patients with immunological disorder comprising:

administering an efficient amount of the pharmaceutical composition according to claim 4, to said patients.

18. The method according to claim 17, wherein said immunological disorder is one selected from the group consisting of allergic rhinitis, allergic conjunctivitis, allergic asthma, atopic dermatitis, food allergy, hyper IgE syndrome, atopic eczema, and rheumatoid arthritis.

19. A method of treating patients with immunological disorder comprising:

administering efficient amount of the pharmaceutical composition according to claim 8 said patients.

20. The method according to claim 19, wherein said immunological disorder is one selected from the group consisting of allergic rhinitis, allergic conjunctivitis, allergic asthma, atopic dermatitis, food allergy, hyper IgE syndrome, atopic eczema, and rheumatoid arthritis.

21. An immunological disorder drug comprising an effective amount of the pharmaceutical composition according to claim 3.

22. An immunological disorder drug comprising an effective amount of the pharmaceutical composition according to claim 7.

23. A pharmaceutical composition for treating immunological disorder comprising an effective amount of:

an aqueous extract of *Tuber Ophiopogonis;* powder of *Tuber Pinelliae;* powder of *Radix Glycyrrhizae;* powder of *Radix Panacis Quinquefolii;* and powder of *Herba Tridacis procumbentis.*

24. The pharmaceutical composition according to claim 23, wherein said *Tuber Ophiopogonis,* said *Tuber Pinelliae,* said *Radix Glycyrrhizae,* said *Radix Panacis Quinquefolii,* and said *Herba Tridacis procumbentis* are at a weight ratio of 3:2:1:1:1.

* * * * *